United States Patent [19]
Krause

[11] Patent Number: 5,463,228
[45] Date of Patent: Oct. 31, 1995

[54] APPARATUS FOR THE DETECTION OF A FLUID PHASE BOUNDARY IN A TRANSPARENT MEASURING TUBE AND FOR THE AUTOMATIC EXACT METERING OF AN AMOUNT OF LIQUID

[75] Inventor: Friedemann Krause, Feldafing, Germany

[73] Assignee: Boehringer Mannheim GmbH, Mannheim, Germany

[21] Appl. No.: 165,859

[22] Filed: Dec. 14, 1993

[30] Foreign Application Priority Data

Dec. 19, 1992 [DE] Germany ............. 42 43 247.2

[51] Int. Cl.$^6$ ............. G01F 23/28; G01B 11/02
[52] U.S. Cl. ............. 250/577; 340/619
[58] Field of Search ............. 250/577; 340/619; 356/375

[56] References Cited

U.S. PATENT DOCUMENTS 4,740,077  4/1988  Goodwill ............. 356/23

FOREIGN PATENT DOCUMENTS

| | | |
|---|---|---|
| 146489 | 7/1936 | Austria ............. 340/619 |
| 0014120A1 | 8/1980 | European Pat. Off. . |
| 0185285A2* | 6/1986 | European Pat. Off. . |
| 0250671B1 | 1/1992 | European Pat. Off. . |
| 0541501A1 | 5/1993 | European Pat. Off. . |
| 2496259 | 6/1982 | France . |
| 2855651C2 | 10/1983 | Germany . |
| 3605403A1 | 5/1987 | Germany . |
| 3737204 | 5/1989 | Germany . |
| 3515890C2 | 12/1989 | Germany . |
| 4026228C1 | 8/1991 | Germany . |
| 8400518 | 2/1984 | Netherlands . |
| 2256478 | 12/1992 | United Kingdom . |

OTHER PUBLICATIONS

"Optical Device for the Measurment of Small Volume Changes", by A. K. Davies et al, Applied Optics, vol. 25, No. 7, Apr. 1, 1986, pp. 1245–1246.

Patent Abstracts of Japan, vol. 9, No. 232 (P–389), Sep. 18, 1985.

The Steam Engineer, Bd. 25, Nr. 291, Dec. 1955, p. 108, "Hopkinsons Remote Water Level Television System".

*Primary Examiner*—Richard A. Rosenberger
*Attorney, Agent, or Firm*—Nikaido, Marmelstein, Murray & Oram

[57] ABSTRACT

Apparatus for the detection of a phase boundary (10) in a transparent measuring tube (9), in particular of a liquid level in a rising tube (11) (LLD, Liquid Level Detector). The rising tube (11) is illuminated by an illumination device (15) and the light passing through the rising tube (11) is received by a light reception device (17) which converts it into signals dependent on the spatial distribution of the light intensity. A data processing unit (7) is used for processing the signals from the light reception device (17) into information on the height of the liquid level (10) in the rising tube (11). In such an apparatus very accurate detection can be achieved even for weakly and differently coloured liquids in very thin capillary-shaped rising tubes by means of an illumination device (15) which is designed for the spatially steady illumination of the rising tube (11), in particular with diffuse light, the light reception device (17) comprising an optical imaging system (18) for generating an image of the rising tube (11) in an image plane (19) and a row (20) of closely spaced light-sensitive elements in the image plane.

14 Claims, 4 Drawing Sheets

APPARATUS FOR THE DETECTION OF A FLUID PHASE BOUNDARY IN A TRANSPARENT MEASURING TUBE AND FOR THE AUTOMATIC EXACT METERING OF AN AMOUNT OF LIQUID

The invention relates to an apparatus for the detection of a fluid phase boundary in a transparent measuring tube as well as an apparatus equipped with such a detection means for the automatic exact metering of small amounts of liquid.

Means for the detection of a fluid phase boundary in a measuring tube are frequently required. A fluid phase boundary is understood to be any boundary surface between a liquid and an optically distinguishable phase, which may be gaseous, liquid or even solid and which is in phase boundary contact with the liquid.

Particularly common are means for the detection of the level of a liquid in a measuring tube, which stands upright and can be referred to as a rising tube. Such means are also termed according to a common English expression, as LLDs (Liquid Level Detectors). The invention is directed in particular towards applications in devices for the analysis of body liquids (in particular blood and urine) where the fluid phase boundary of samples or liquid reagents has to be detected.

If the liquid is contained in an open vessel, its level can be detected by means of a probe immersed from above, the probe being in most cases simultaneously the tip of a pipette, by means of which a reagent or sample liquid may be supplied or extracted. At the tip of the probe or of the pipette there is located a liquid detector, which upon immersion—in some cases immediately prior to immersion—into the liquid generates a signal. Various principles are known for this, which are based for example on the determination of the electrical resistance or the electrical capacitance between two electrodes attached to the tip of the pipette. Optical principles have also been discussed for such applications (European patent 0 250 671). With these methods the position of the probe or pipette on immersion in the liquid provides a measure for the height of the liquid level.

The invention is directed in particular, but not exclusively, towards the determination of the fluid phase boundary in a rising tube sealed at the top. Optical measuring principles have been proposed for such applications, in which the rising tube is illuminated with an illumination device comprising at least one light source. A light reception device with at least one light detector receives light passing through the rising tube and converts it into electrical signals dependent on the spatial distribution of the intensity of the light. The signals from the light reception device are supplied to a data processing unit, in order to derive the desired information on the height of the liquid level in the rising tube.

The implementation of this seemingly simple principle causes considerable problems, in particular if the level in a capillary with a very thin inner bore has to be determined with high precision.

In German patent specification 28 55 651 the problems encountered with the various known optical measurement principles (determination of the darkening through a coloured liquid or the brightening through a clear liquid; meniscus scanning; reflection or scattered light principle) are discussed. A particular electronic circuit is proposed, in order to offset the optical problems by improvements in the signal processing.

In medical analysis units the problems of liquid detection are aggravated by the fact that the reagents and samples are generally very slightly coloured. In addition, the coloration varies from sample to sample and from reagent to reagent, and yet the level has to be determined exactly irrespective of these differences. In German patent specification 28 55 651 it is pointed out that an earlier proposal for solving this problem makes use of the cylindrical lens effect of the liquid contained in the rising tube. For example, the light focused through the liquid-filled tube may be kept separate from the photocell by means of a diaphragm. If the liquid level in the rising tube falls to such an extent that the relevant region in the tube is empty, the focal length of this cylindrical lens changes, and a part of the light impinges on the photocell.

In European patent application 0 185 285 the problem of the detection of a substantially transparent medical liquid is also discussed. Again the principle described in the preceding paragraph is used the liquid-filled rising tube serving in this case as a lens for focusing a narrow band of light onto a surface opposite the light source (relative to the rising tube). It is important here that the rising tube has a particular (cylindrical) shape and that the geometrical conditions of the focusing are precisely met. In one embodiment the light reception device comprises a plurality of light receivers in the form of photocells, photoresistors, photodiodes, phototransistors or similar, which are arranged in each case opposite a light transmitter in a parallel arrangement so that they form a large number of light barriers arranged closely above one another. Although this arrangement allows convenient recording of the level, it meets only modest requirements as regards the resolution and precision of the level determination. A spacing between the light-sensitive elements of 1 mm is utilized and an accuracy of the volume determination in the rising tube of about 100 μm achieved. From these data it becomes apparent that a relatively thick rising tube with an inner bore of about 5 mm was used. The principle of this European patent application, which is based on the different degrees of focusing of the filled and the empty measuring tube, is not suitable for the detection of the phase boundary in a capillary-shaped measuring tube with an inner bore of for example less than 1 mm.

In an apparatus described in German patent application 36 05 403 the detection of the liquid level is based on the fact that a continuous transition of the measured light intensity is achieved in the region of the liquid level. In this case use is made of a linear light source positioned parallel with the rising tube in conjunction with a row of detectors arranged directly on the rising tube. It is regarded as absolutely essential that the detected light intensity differs between the liquid-filled and the gas-filled region of the rising tube. Said difference is ensured either by the liquid being dyed or (as with the means described above) by the cylindrical lens effect during passage of the light through the rising tube.

In the scientific article "Optical device for the measurement of small volume changes" by A. K. Davies et al., Applied Optics, 1986, 1245 f., a means is described which is to be used for recording the level (and hence the volume) in a capillary tube of 50 μl volume. This proposal requires sophisticated equipment. The light is filtered in narrow bands. A specific angle of incidence (28°) at which the light impinges on the capillary has to be selected. Additionally the photocell positioned behind the capillary has to be screened by means of a specific arrangement of diaphragms. Despite this, the detection of the phase boundary between liquid and air is not possible in all regions of the capillary. Rather only the central 20% of the capillary is used. The principle, based on the analysis of the variation of an analog signal, requires precise calibration.

In order to allow an accurate, reliable determination of the position of the phase boundary, in particular in a measuring tube with a very small (capillary) bore (in particular in cases where the optical brightness of the media on the two sides of the phase boundary differs only slightly, if at all), the invention is directed according to a first main aspect towards an apparatus for the detection of a fluid phase boundary in a transparent measuring tube with an illumination device with at least one light source for illuminating the measuring tube, a light reception device with at least one light detector, which receives light passing through the measuring tube and converts it into electric signals dependent on the spatial distribution of the light intensity, and a data processing unit for processing the signals from the light reception device into information on the position of the liquid phase boundary in the measuring tube, in which the illumination device is designed for the spatially steady or evenly distributed illumination of a detection section of the measuring tube and the light reception device comprises an optical imaging system generating an image of the detection section in an image plane and a row of light-sensitive elements positioned closely together in the image plane.

The optical imaging system preferably is an optical lens and the light-sensitive elements are preferably a linear array of CCD elements (charged coupled devices). The spacing of the light-sensitive elements is preferably less than 50 μm.

According to the invention the position of a fluid phase boundary in a measuring tube with a very small bore of less than 1 mm, particularly preferably even less than 0.5 mm, may be reliably and accurately detected.

The invention allows the determination of the position of the fluid phase boundary in thin capillary tubes of this kind without moving parts. Because of the fact that the liquid column in the measuring tube is detected with high resolution in a fairly long detection section, it is in addition possible to eliminate typical sources of error, such as air bubbles or impurities, by means of a detection algorithm carried out by a microprocessor-controlled data processing unit.

The illumination of the detection section must be spatially steady or evenly distributed in the sense that (in contrast to light barriers) no sudden changes in the spatial distribution of the illumination intensity occur. A steady illumination of this kind can be achieved by various known means, for example by means of a longitudinally extended (for example tube-shaped) light source positioned parallel with the measuring tube, a large number of light sources arranged closely to one another and parallel with the measuring tube or an illumination lens system which spreads the light from a single light source (e.g. a halogen lamp) in a suitable manner. The main preference, however, is for an embodiment in which the illumination device comprises a light scattering device, in particular with a mat lighting plate such as a ground-glass disc (or another diffusion surface) positioned parallel with the measuring tube. Thus with an inexpensive design and without precise positioning of the light source a particularly accurate detection of the phase boundary is achieved.

The construction is relatively simple. No diaphragms, filters or shields are required. An exceptionally high level of accuracy and precision may be achieved. For example, volume differences of ±1 nl have been reliably detected with the invention in a capillary with an inner bore of 0.2 mm and a spacing of the CCD elements (pixel) of 25 μm.

The system operates without moving parts and in real time. It is possible to record accurately the variation of the position of the phase boundary in time and to determine for example its rate of movement.

According to a second main aspect the invention is directed towards a means for the automatic exact metering of small amounts of liquid, in which an LLD (or other phase boundary detector) is used which is constructed preferably, but not necessarily, according to the first main aspect.

The invention is also directed towards an apparatus for the automatic exact metering of small amounts of liquid. Such apparatus are also described as (automatic) pipettors. They are used widely in connection with the analysis of body liquids, in particular with corresponding analysis instruments for the transfer of samples and reagents from one vessel into another vessel. Generally the metering of the liquid is based on the movement of a piston in a precision tube. The piston is driven by a stepping motor, whose movement is transferred to a spindle drive via a toothed belt. Said spindle drive moves a carriage which is usually connected firmly to the piston. The precision of the metering with such a piston pump is dependent on the precision of the stepping motor and the accuracy of the transfer elements (toothed belt, spindle drive). In order to ensure high precision, the mechanical parts have to be manufactured very accurately and are consequently expensive. The mechanically movable parts may wear and, in order to ensure the accuracy, have to be serviced regularly. Additional errors with respect to the metering precision may result from differences in the consistency, the viscosity or the fat content of the liquid to be metered. Such differences are particularly pronounced in the case of blood and the reagent liquids commonly used in medical analysis, which contain proteins and other giant molecules.

In order to provide an automatic pipettor with high accuracy, in particular for the metering of very small sample volumes, the invention is directed according to a second main aspect towards a means for the automatic direct metering of small amounts of liquid. It comprises a phase boundary detection means (PBDM), by means of which a fluid phase boundary in a measuring tube is automatically detected and an electrical signal corresponding to the position of the phase boundary in a detection section of the measuring tube is generated. A liquid transfer opening for the aspiration and ejection of liquid is in fluid communication with a first end of the measuring tube. An auxiliary fluid transfer means (AFTM) for the precisely controlled supply and withdrawal of an auxiliary fluid to and from the measuring tube is in fluid communication with a second end of the measuring tube. It comprises auxiliary fluid supply means (AFSM) and auxiliary fluid withdrawal means (AFWM). An electronic control unit is provided, for activating the auxiliary fluid transfer means as a function of the signal of the phase boundary detection means in such a way that by withdrawal or supply of auxiliary fluid to the measuring tube precisely defined amounts of liquid are aspirated or ejected.

The fluid phase boundary detection means preferably is designed according to the first main aspect of the invention. A thin capillary tube may be used as the measuring tube, which is immersed directly in the liquid, the height of the liquid level being determined precisely with the LLD according to the first main aspect of the invention at a relatively short distance above the suction opening. Since the capillary tube may serve as the pipetting tip the sample volume may be measured directly therein and the aspirated volume is determined directly and immediately. Various conditions such as air pressure, ambient temperature or viscosity of the liquid have practically no influence on the metering accuracy.

The measuring tube may be a single use (disposable)

capillary which is inserted into an automatic mounting of the pipettor. In this way the risk of the carry-over of liquid residues to the next volume of liquid to be metered is completely avoided. With previously known designs disposable pipette tips on automatic pipettors have caused major accuracy problems in the pipetting of very small volumes which were due to unavoidable differences in the coupling of the pipettor.

In principle, however, the pipettor according to the second main aspect of the invention may also be used with some other LLD, which automatically detects the level of a liquid in a rising tube sealed at the top and generates a resulting electrical signal which is passed to the control unit in order to monitor precisely the aspiration and ejection of the liquid. Known means of this kind have been mentioned before.

The auxiliary fluid may be a gas or a liquid. A liquid may be supplied or withdrawn in a precisely controlled manner by means of a piston pump. If the auxiliary fluid is not miscible with the liquid to be metered, a direct contact may exist between the two liquids at the phase boundary. A miscible liquid may also be employed if a gas bubble is aspirated between the auxiliary liquid and the liquid to be metered. Separation of two different liquids by means of a gas bubble is common in analytical procedures. In this case one of the phase boundaries between the gas bubble and the liquid to be metered or the auxiliary liquid is detected.

In a further preferred embodiment the auxiliary fluid is a gas, in particular air, and the measuring tube is positioned substantially vertically as a rising tube. Here the phase boundary is the liquid level which separates the liquid column in the rising tube from the gas space that is located above it to which the gaseous auxiliary fluid is supplied or from which it is withdrawn. The transfer device for the auxiliary fluid preferably comprises a change-over valve unit which may consist of a multi-way valve or a plurality of individual two-way valves. In each case at least one shut-off valve (i.e. a valve which changes rapidly between an open and a closed position) should be arranged near to the upper end of the rising tube.

The automatic pipettor according to the invention is particularly suitable for the fully automatic pipetting of very small amounts of liquid (in the range between 20 nl and 20 µl, i.e. $2 \times 10^{-8}$ l to $2 \times 10^{-5}$ l). Very high precision is achieved here. At 100 nl metering volume the maximum variation coefficient (VC) is for example 1% (i.e. $10^{-9}$ l). The measuring tube may be a thin capillary with an inner bore between 0.1 mm and 0.3 mm, which is immersed directly in the liquid to be pipetted (i.e. the liquid transfer opening is a part of the measuring tube).

The monitoring of a metered amount of liquid by means of an optical LLD is known from German patent specification 35 15 890. The means described there permits only a comparatively little precision in metering a relatively large amount of liquid (0.3 ml=300 µl). The operation differs fundamentally from the means described here. In particular the liquid is withdrawn from the measuring tube by means of an injector spray nozzle connected downstream of the measuring tube. Neither means for the supplying nor means for the withdrawal of an auxiliary fluid are connected to the measuring tube. With the previously known means it is not possible to carry out a rapid metering of a succession of different liquids largely without carry-over, as is required in the case of clinical analysis units. Likewise it is impossible to meter with it liquids which are present in very small amounts and therefore have to be metered practically without any dead volume.

The operation of the automatic pipettor according to the invention is not affected by mechanical wear. The valves are subject to only slight wear, which does not affect their operation during a long service life. If according to a preferred embodiment a gas pump is used as a gas suction means and/or gas supply means, the latter is also subject to mechanical wear, which is however insignificant for the precision of the metering. A simple and relatively inexpensive gas pump may be used.

In addition a permanent check is possible to see whether the amount of liquid aspirated or ejected agrees with the desired predetermined amount. With conventional automatic pipettors, on the other hand, errors can occur, for example through clogging of the needle or because the stepping motor "loses" individual steps which is not recognized or recognized only with expensive additional equipment.

The means according to the invention operates satisfactorily with different metering liquids, in particular blood, serum and protein-containing reagent liquids, even if the latter differ considerably in their composition, viscosity and hydrophility properties (surface tension). Changing the liquids has practically no effect on the pipetting accuracy. In contrast to conventional pipettors changes in the environmental conditions (for example temperature changes) may be taken into account relatively easily in the control algorithm and hence eliminated.

The invention will be explained in detail below by means of an exemplifying embodiment shown diagrammatically in the figures, where FIG. 1 shows a diagramatic view of an automatic pipettor with liquid level detection means;

Figure 1:
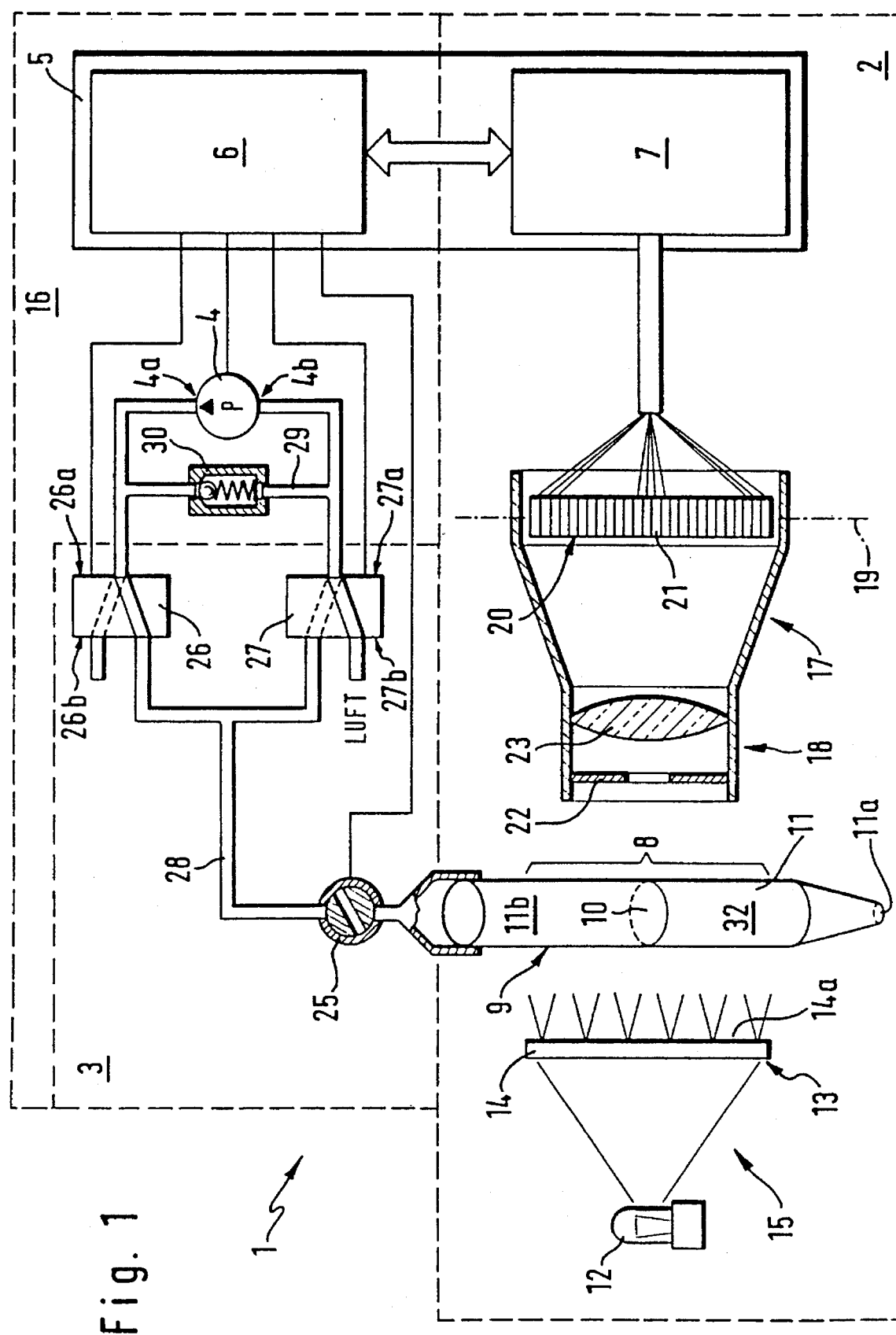

The automatic pipettor 1 shown in FIG. 1 consists mainly of a detection means 2 for the detection of a fluid phase boundary 10 in the detection section 8 of a measuring tube 9, and an auxiliary fluid transfer means 16, comprising a change-over valve unit 3 and a gas pump 4. An electronic central unit 5 includes a control unit 6 for the gas pump 4 and the change over valve unit 3 as well as an data processing unit 7 for the detection means 2.

In the exemplified embodiment the detection means 2 is a liquid level detector (LLD), i.e. the phase boundary 10 is the boundary between the air and the liquid in a measuring tube 9 designed as a vertical rising tube 11. The LLD serves for the automatic detection of the liquid level 10 in the rising tube 11. To this end the rising tube 11 is illuminated with diffuse light from a light source 12 via a light scattering device 13. The light scattering device 13 is in the case shown a ground-glass plate 14. The rising tube 11 is positioned on the side of the ground-glass plate 14 facing away from the light source 12. The ground-glass plate 14 and the rising tube 11 are disposed roughly parallel with one another. The light source 12 and the light scattering device 13 together form an illumination device 15 for the illumination of the rising tube 11.

On the side of the rising tube 11 opposite the illumination device 15 there is located a light reception device 17, which consists of an optical imaging system 18 for the imaging of the rising tube into an image plane 19 and a row 20 of light-sensitive elements arranged in an image plane 19, which in the preferred case shown are CCD elements (pixels) 21.

The light source 12 may consist of one or more lamps, for example halogen lamps, tungsten lamps or similar. The light scattering device is preferably a mat lighting plate illuminated from the rear side, but the diffuse illumination of the rising tube 11 which is preferred in the context of the invention may for example also be accomplished with a diffusely reflecting surface which is illuminated from the side in such a way that preferably no light from the light source falls directly onto the rising tube 11. Both in the case of a mat lighting plate and in the case of a diffusely reflecting surface, the surface facing the rising tube 11, which may be designated as the diffusion surface 14a, should be positioned at a uniform distance from (i.e. roughly parallel with) the latter.

The rising tube 11 is preferably a capillary with an inner bore of less than 1 mm, particularly preferably less than 0.5 mm. Its bottom end is in fluid communication with a liquid transfer opening 11a through which the liquid may be aspirated and ejected. The words "in fluid communication" are to be taken here to mean that the liquid transfer opening 11a may—as shown—be an opening in the rising tube 11 itself or else be in indirect communication with the rising tube 11 by means of a tube or hose.

The optical imaging system 18 consists with expediency of a diaphragm 22 and a photographic lens 23 (shown only as a simple lens in the drawing).

The row of light-sensitive elements may in certain circumstances also be part of a two-dimensional array which extends not only parallel with the rising tube 11, but also perpendicular thereto in the image plane 19. However, a purely linear arrangement of the CCD pixels, with a spacing of less than 50 µm, preferably not more than 25 µm, has also proved sufficient and particularly expedient.

In the embodiment shown the light source 12, the rising tube 11 and the row 20 of the CCD pixels 21 are located in the same plane. With said arrangement (and metering of a clear liquid) CCD pixels onto which the liquid-filled region of the capillary is imaged supply a higher output signal than the pixels onto which the air-filled region of the capillary is imaged.

Figure 2:
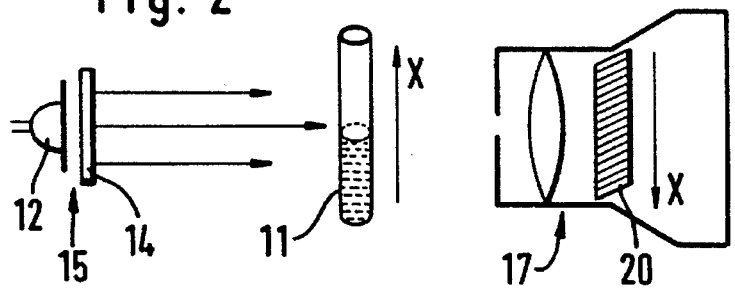
FIG. 2 to FIG. 5 show diagramatic views of various arrangements of the illumination means and of the light reception means in a liquid level detection means according to the invention.
Figure 2:
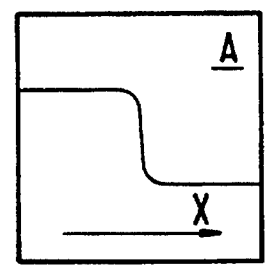

This state of affairs is illustrated in FIG. 2 which shows, next to a view of the LLD corresponding to FIG. 1, a graph A of the output signals of the CCD pixels 21 in relation to the location X of the capillary rising tube 11 which is imaged thereon.

The graph A, however, shows said relation in a highly simplified form. In reality the signal differences are far smaller.

In a test setup of the invention a 12.5 cm long capillary with an inner bore of 400 µm was used as the rising tube 11. A halogen lamp served as the light source 12, and the light scattering device 13 was a ground-glass disc which was positioned at a distance of 7 cm parallel with the rising tube 11. The row 20 of light-sensitive elements consisted of a CCD line sensor with 1024 pixels with a size of 0.025 mm×1 mm. A camera lens with f=1.8 and 50 mm focal length was used as the optical imaging system. The distance between the light source 12 and the image plane 19 was about 20 cm, the rising tube 11 being arranged approximately in the centre.

The output signal of the CCD line sensor was transferred via an interface to a standard personal computer which served as the data processing unit 7. The assignment of the CCD output signals to the values "capillary filled" or "capillary empty" was accomplished by comparison with a suitably positioned threshold value. The interface should allow parallel processing of the data, so that the detection of the liquid level in real time is ensured.

With this setup it was possible to detect the air-liquid transition in the rising tube 11 with an accuracy of ±1 pixel.

Further experiments have shown that with additional optimizing measures, in particular a magnifying optical imaging system 18, and by the use of a CCD line with smaller pixel spacing the resolution during the detection of the liquid level 10 in the rising tube 11 may be still further improved. This applies even to capillaries with an inner bore of 0.2 mm when the overall setup shown in FIGS. 1 and 2 is used. Volume differences of less than ±1 nl may be detected. This favourable result must be regarded as surprising given the difficult conditions, in particular in the detection of the level of a colourless liquid. This is also confirmed by the fact that in the prior art described above considerably more expensive methods are used and nevertheless far worse results obtained.

Figure 3:
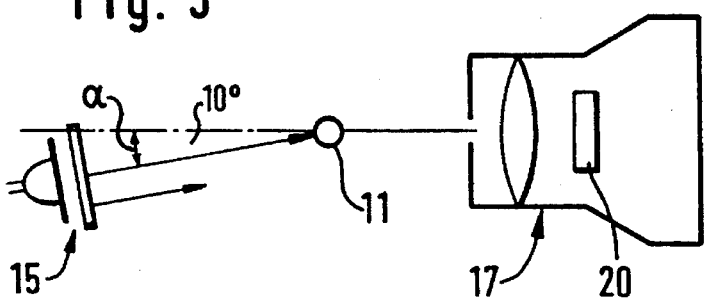
Figure 3:
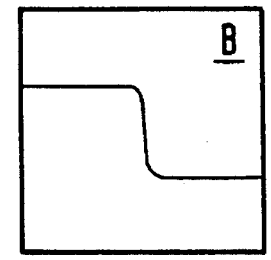
Figure 4:
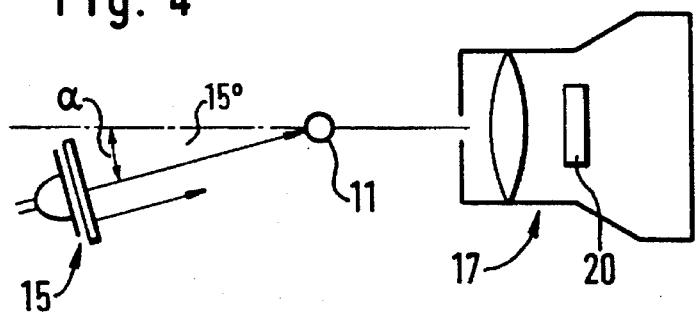
Figure 4:
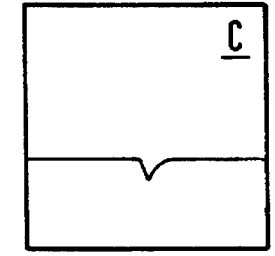
Figure 5:
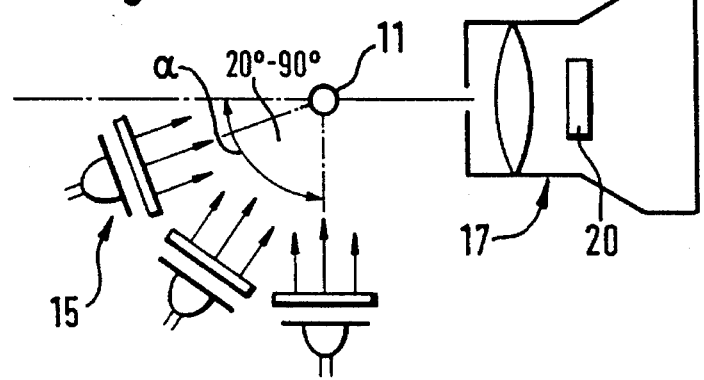
Figure 5:
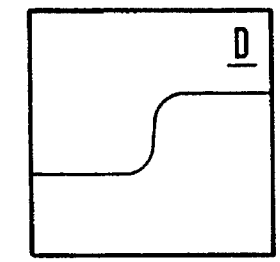

The graphs B, C, D of FIGS. 3 to 5 illustrate the dependence of the test signal on the angular position of the light source 12 and of the light scattering device 13. A top view is shown in each case, and the axis of the rising tube 11 therefore runs at right angles to the plane of projection. If the azimuth angle $\alpha$ (referred to a plane perpendicular to the rising tube 11) shown in the figures is changed, the difference in the pixel output signals, which correspond to the liquid-filled and the air-filled sections of the rising tube 11, is reduced.

In the case shown the difference between the liquid-filled and the air-filled capillary diminishes more markedly with azimuth angles $\alpha$ of more than 10°. With angles above 15° the relationship is reversed: CCD pixels onto which the image of the air-filled section of the rising tube 11 is imaged have a higher output signal than those which correspond to the liquid-filled section of the capillary. In a second angular range between 20° and 30°, which is shown in FIG. 5, there is again a signal difference. It is somewhat less in this range, however, than in the case of the arrangement in the same plane according to FIG. 2.

If the test setup is arranged so that the brightness of the liquid-filled and of the gas-filled sub-sections of the measuring section of the rising tube 11 differs significantly (as with FIGS. 2, 3 and 5), the analysis of the output signal of the row 20 of light-sensitive elements 21 is particularly simple. As mentioned, it is generally sufficient to set a threshold value so that it lies approximately in the centre between the output signals that correspond to the filled and to the empty capillary. Very good accuracy may be achieved in this way without high-precision adjustment of the components. As is seen diagrammatically in FIGS. 2 to 5, the intensities vary only slightly over comparatively wide angular ranges.

A slight tilting of up to 10° of the illumination means 15 about a horizontal axis (running in the plane of projection of FIGS. 3 to 5) also does not affect the quality of the detection to a significant extent. This is a further illustration of the tolerance of the described system with respect to positioning inaccuracies.

A particular advantage of the phase boundary detection means (PBDM) according to the invention is that it allows precise locating of the phase boundary even in cases where the brightness of the regions of the measuring tube neighbouring the phase boundary does not differ or does so only very slightly.

Figure 6:
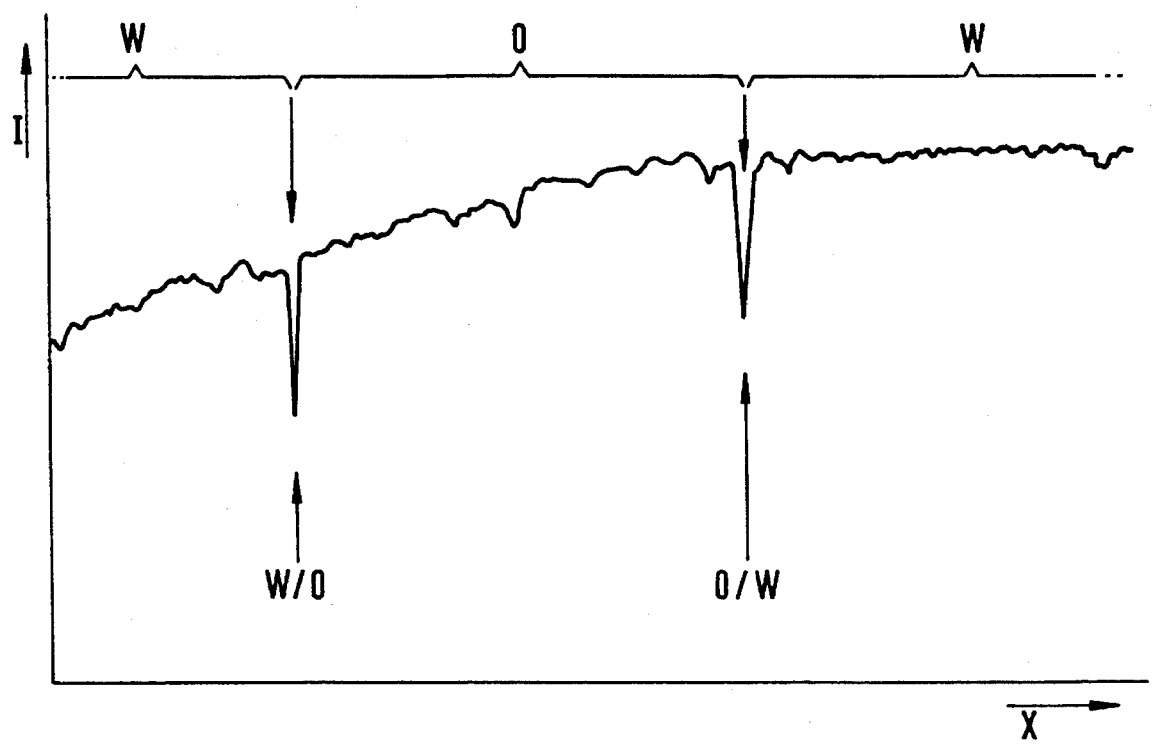
FIG. 6 shows a measurement curve of an intensity distribution as a function of the position of the light-sensitive element in the image plane and FIG. 7 shows a practical embodiment of an apparatus according to FIG. 1 in side elevation.

FIG. 6 shows the signal of the CCD pixels in an experiment in which the measuring section 8 of a measuring tube 9 which is imaged onto the CCDs contains in successive sub-sections water (W), silane-oil (O) and again water (W). The oil does not mix with water, so that phase boundaries W/O and O/W are formed between the water and the oil.

The curve of the intensity I plotted against the measuring location X is slightly curved in FIG. 6. This can be attributed to the fact that the illumination of the detection section was not completely constant in the experiment on which this figure is based, but increased slightly from bottom to top. This is without significance for the analytical accuracy provided a suitable data processing method (such as that described below, for example) is used. It is essential, however, that the illumination is spatially steady as already explained.

It can be seen from the figure that the intensities measured practically do not differ in the oil and in the water in the vicinity of the phase boundaries. At the phase boundary itself there are nevertheless found easily detectable minima of the intensity, which may be analyzed by the data processing unit in order to detect the site of the phase boundary. To this end the measured output signals of the CCD pixels are preferably first subjected to digital low-pass filtering. Such methods, for example with the aid of a Hamming, Blackman or Hanning window function, are known. They lead to a smoothing of the signal curve. In this way false indications of a phase boundary based on accidental signal fluctuations are avoided.

In the filtered signal curve the signal minimum may be determined again by means of a threshold value. The latter is positioned preferably by a multiple of the statistical fluctuation range of the pixel signals below the mean signal value of a defined neighbourhood (of for example 10 pixels). An intensity lying beneath said threshold value is recognized as the phase boundary.

In order to still further improve the detection of the phase boundary in critical cases, it may be expedient to differentiate the filtered signal curve and to place a threshold for the recognition of the phase boundary in the signal curve resulting therefrom (i.e. in the first derivative of the measured signal curve).

As mentioned, the automatic pipettor 1 shown in FIG. 1 contains in addition to the LLD 2 the change-over valve unit 3, the gas pump 4 and the associated control unit 6. The change-over valve unit 3 consists in the preferred embodiment shown of a rapid shut-off valve 25 and two two-way switching valves 26 and 27.

The valves 26, 27 each comprise on a first side 26a, 27a a coupling and on a second side 26b, 27b two couplings. By switching of the valve optionally a connection between the one coupling of the first side and one of the couplings of the second side is produced. The first side 26a of the valve 26 is connected to the delivery side 4a of the gas pump 4, while the first side 27a of the valve 27 is in communication with the suction side 4b of the gas pump.

One of each of the two couplings of the second side of the valves 26, 27 is coupled to a Y-piping system 28, by means of which a connection to a coupling of the shut-off valve 25 is produced, namely the coupling facing away from the rising tube 11. The other coupling of the second side 26b, 27b of the valves 26, 27 is connected to the external air in each case. The valves 26, 27 are switched synchronously so that in a first position (shown in continuous lines in the figure) the delivery side of the gas pump 4 is connected to the shut-off valve 25, while in a second position (shown in dashes in the figure) the suction side 4b is connected to the shut-off valve 25. In order to limit the pressure produced by the gas pump 4, a bypass 29 with at least one pressure relief valve 30 is provided.

In order to aspirate liquid through the liquid transfer opening 11a into the rising tube 11, the reversing valves 26, 27 are brought into the position shown in dashes, so that a vacuum generated by the gas pump is applied to the shut-off valve 25. When this valve is opened a connection to the gas space 11b of the rising tube 11 above the liquid level 10 is provided. The liquid is aspirated and the liquid level 10 rises under the supervision of the LLD 2. As soon as the liquid level 10 has reached a height corresponding to the desired suction volume, the valve 25 is closed. The valve control signal is produced by the control unit 6, as a function of an electrical signal generated by the data processing unit 7 and corresponding to the height of the liquid level 10, by comparison with a target value corresponding to the desired level.

Surprisingly it has been found, that with such an arrangement the liquid level 10 may be brought into a defined position with very high precision. It is important however that a sufficiently rapid shut-off valve 25 is used. A rapid solenoid valve (Lee valve) with a switching frequency of 2000 Hz has proved effective in practice. In addition the shut-off valve 25 should be positioned as close as possible to the upper end of the rising tube. The dead volume between the upper end of the detection section 8 and the shut-off valve 25 should preferably not be greater than the inner volume of the detection section 8 of the measuring tube 9.

The change-over valve unit 3 may, as the skilled person will be aware, also be constructed in another manner, for example with the aid of a four-way valve or with four one-way valves, which are switched synchronously so that gas is supplied to the gas space 11b or withdrawn from it at the desired time.

In the embodiment shown in FIG. 1 the aspiration into the measuring tube 9 or the ejection out of the measuring tube 9 is controlled by the supply or discharge of a gas as auxiliary fluid. The phase boundary 10 is here a boundary surface between the liquid column 32 situated in the bottom part of the measuring tube 9 and the air contained in the gas space 11b. Alternatively, however, a liquid may, as mentioned, be used instead of the gas. In such a metering means a liquid pump (for example a piston pump) would be provided in place of the gas pump, which draws in liquid from a liquid storage tank and discharges it into the same or a different tank. Although various fluids (gases or liquids) may be used as an auxiliary fluid to draw the liquid to be metered into the measuring tube 9 or to eject it from the latter, the embodiment with a gas (in particular air) is particularly preferable, because it is particularly simple and eliminates any contact of the liquid to be metered with another liquid.

Figure 7:
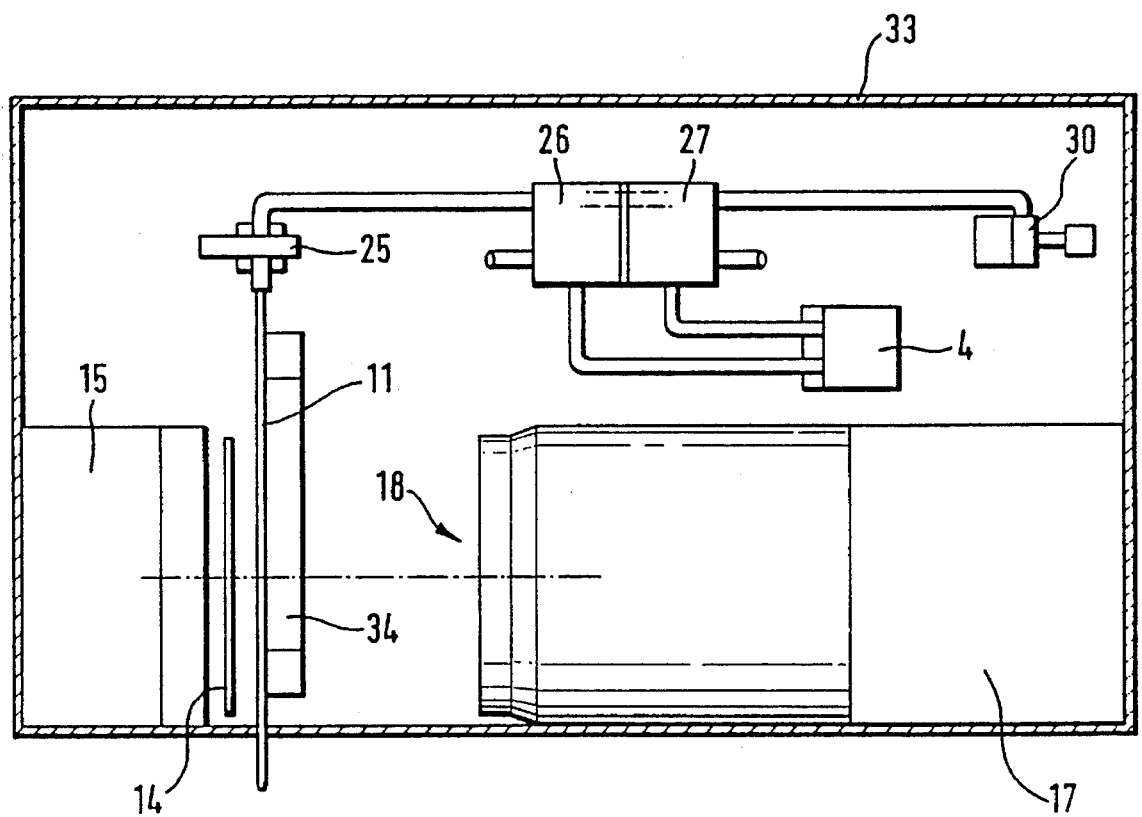

In the practical embodiment of an automatic pipetting means shown in FIG. 7 the components are secured to a common frame 33. The illumination means 15 has a light-tight closed casing in which the light source (not shown) is located. The ground-glass disc 14 is fixed to the side of the illumination means 15 facing the rising tube 11. The light reception means 17 is also accommodated together with the optical imaging system 18 in a common light-tight closed casing. The connecting lines between the gas pump 4, the change-over valves 25, 26, the pressure relief valve 30 and the solenoid valve 25 are formed by hoses. The rising tube 11 is a very thin capillary which is secured to the frame 33 by means of a carrier part 34.

In the embodiment shown the rising tube 11 is fixed. It can therefore not be moved upwards and downwards during the pipetting procedures. If such a movement is desired, it can be achieved in the context of the present invention by moving rising tube 11 upwards and downwards in an exactly predetermined and measurable manner, said movement being taken into account by the data processing unit 7 in the calculation of the height (and of the resulting volume) in the rising tube. A second possibility is to use a fixed rising tube and connecting a separately movable pipetting needle at its bottom end to the liquid transfer opening, via a flexible hose.

I claim:

1. An apparatus for automatic exact dosing of small amounts of liquid in a medical analysis system, said apparatus comprising:

a transparent measuring tube, said measuring tube comprising a capillary tube having an inner diameter of less than 1 mm, said measuring tube also including a liquid transfer opening at a first end thereof, said liquid transfer opening for aspiration of fluid;

a fluid phase boundary detection means for automatically detecting a fluid phase boundary in said measuring tube, wherein an electrical position signal corresponding to a position of the fluid phase boundary is generated, said fluid phase boundary detection means comprising an illumination device for providing evenly distributed light onto a detection section of the measuring tube, said illumination device including at least one light source for illuminating said measuring tube, light reception means for receiving light from said illumination device, said light reception means detecting light passing through said measuring tube from said illumination device, said light reception means including at least one light detector and an optical imaging system for generating an image of the detection section in an image plane, and a plurality of closely spaced light-sensitive elements in the image plane; said fluid phase boundary detection means further comprising data processing means for processing signals from the at least one light detector into the electrical position signal indicating the position of the fluid phase boundary in the measuring tube; said apparatus further comprising electronic control means for controlling aspiration and withdrawal of the fluid from the measuring tube in precisely defined amounts based upon the electrical position signal corresponding to the position of the fluid phase boundary in the measuring tube, wherein a position of the fluid phase boundary in the detection section of the measuring tube is detected by the data processing means from a signal curve of the signals of the at least one light detector being dependent upon a spatial distribution of the intensity of the received light.

2. An apparatus as recited in claim 1, wherein said light-sensitive elements comprise CCDs.

3. An apparatus as recited in claim 1, wherein said light-sensitive elements are spaced by a distance of less than 50 µm.

4. An apparatus as recited in claim 1, wherein said measuring tube comprises a capillary tube having an inner diameter of less than 0.5 mm.

5. An apparatus as recited in claim 1, wherein said illumination device further comprises a light scattering device for illuminating the detection section of the measuring tube with diffused light.

6. An apparatus as recited in claim 5, wherein said light scattering device comprises a diffusion surface positioned in an essentially parallel relationship with said measuring tube.

7. An apparatus as recited in claim 5, wherein said diffusion surface is a light diffusing lighting plate, and said at least one light source is disposed on a side of the lighting plate facing away from the measuring tube.

8. An apparatus as recited in claim 1, wherein an auxiliary fluid transfer means is coupled to a second end of the measuring tube for a precisely controlled supply and removal of an auxiliary fluid to and from the measuring tube under control of the electronic control means for removal and supply of auxiliary fluid to the measuring tube, and resulting aspiration and ejection of a liquid at the first end of the measuring tube, wherein said auxiliary fluid comprises a gas, and wherein said measuring tube is a rising tube for containing an amount of liquid, and wherein said phase boundary is a liquid level at which an amount of liquid is separated from a gas space therein, the gas space being located above the liquid with the auxiliary fluid being supplied to and discharged from the gas space in order to eject and aspirate precisely defined amounts of liquid.

9. An apparatus as recited in claim 8, wherein said auxiliary fluid comprises a gas, and wherein said measuring tube is a tube for containing an amount of liquid, and said phase boundary is a liquid level at which an amount of liquid is separated from a gas space therein, with the auxiliary fluid being supplied to and discharged from the gas space in order to eject and aspirate precisely defined amounts of liquid.

10. An apparatus as recited in claim 1, wherein said data processing means comprises filter means for smoothing the signal curve of the signals of the at least one light detector by low-pass filtering.

11. An apparatus as recited in claim 10, wherein said data processing means further comprises differentiating means for differentiation of the signal curve of the signals of the at least one light detector.

12. An apparatus as recited in claim 11, wherein said data processing means further comprises threshold means for detection of the liquid phase boundary of the signal curve of the signals of the at least one light detector by threshold detection of the differentiated signal.

13. An apparatus as recited in claim 1, wherein said data processing means further comprises differentiating means for differentiation of the signal curve of the signals of the at least one light detector.

14. An apparatus as recited in claim 13, wherein said data processing means further comprises threshold means for detection of the liquid phase boundary of the signal curve of the signals of the at least one light detector by threshold detection of the differentiated signal.

* * * * *